United States Patent
Masi

(10) Patent No.: US 9,370,470 B2
(45) Date of Patent: *Jun. 21, 2016

(54) INJECTABLE ALLOPLASTIC IMPLANTS AND METHODS OF USE THEREOF

(71) Applicant: Suneva Medical, Inc., Santa Barbara, CA (US)

(72) Inventor: Louis Masi, Longmeadow, MA (US)

(73) Assignee: SUNEVA MEDICAL, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/227,365

(22) Filed: Mar. 27, 2014

(65) Prior Publication Data

US 2015/0258135 A1     Sep. 17, 2015

Related U.S. Application Data

(63) Continuation of application No. 14/211,994, filed on Mar. 14, 2014.

(51) Int. Cl.

| | |
|---|---|
| *A61K 8/02* | (2006.01) |
| *A61K 8/65* | (2006.01) |
| *A61F 2/00* | (2006.01) |
| *A61Q 19/08* | (2006.01) |
| *A61Q 19/00* | (2006.01) |
| *A61K 9/00* | (2006.01) |
| *A61K 31/78* | (2006.01) |
| *A61K 47/42* | (2006.01) |
| *A61L 27/24* | (2006.01) |
| *A61L 27/48* | (2006.01) |
| *C08L 33/12* | (2006.01) |

(52) U.S. Cl.
CPC ............ *A61K 8/0204* (2013.01); *A61F 2/0059* (2013.01); *A61K 8/65* (2013.01); *A61K 9/0024* (2013.01); *A61K 31/78* (2013.01); *A61K 47/42* (2013.01); *A61L 27/24* (2013.01); *A61L 27/48* (2013.01); *A61Q 19/00* (2013.01); *A61Q 19/08* (2013.01); *C08L 33/12* (2013.01)

(58) Field of Classification Search
None
See application file for complete search history.

(56) References Cited

U.S. PATENT DOCUMENTS

| | | | |
|---|---|---|---|
| 4,592,864 | A | 6/1986 | Miyata et al. |
| 5,344,452 | A | 9/1994 | Lemperle |
| 6,436,424 | B1 | 8/2002 | Vogel et al. |
| 7,910,134 | B2 | 3/2011 | Boutros |
| 8,198,245 | B2 | 6/2012 | Niklason et al. |
| 8,338,174 | B2 * | 12/2012 | Ebisawa et al. ............... 435/371 |
| 8,431,141 | B2 | 4/2013 | Boutros |
| 8,475,815 | B2 * | 7/2013 | Boutros ........................ 424/401 |
| 8,586,089 | B2 | 11/2013 | Anderson |
| 2004/0253678 | A1 * | 12/2004 | Hsiao et al. .................. 435/69.1 |
| 2006/0172918 | A1 * | 8/2006 | Sotome et al. ................... 514/2 |
| 2008/0299172 | A1 | 12/2008 | Young et al. |
| 2009/0028817 | A1 | 1/2009 | Niklason et al. |
| 2009/0068271 | A1 * | 3/2009 | DiCarlo et al. ............... 424/489 |
| 2009/0069271 | A1 | 3/2009 | Dicarlo et al. |
| 2011/0269667 | A1 * | 11/2011 | Shoseyov et al. ............... 514/1.8 |
| 2013/0273603 | A1 * | 10/2013 | De Boer ........................ 435/69.1 |
| 2014/0056982 | A1 | 2/2014 | Anderson |
| 2014/0256695 | A1 * | 9/2014 | Nguyen et al. ................. 514/180 |

OTHER PUBLICATIONS

Trudermis product information from olypus Terumo Biomatterials 2011.*
Gorgieva et al. Collagen-vs. Gelatine-Based Biomaterials and their Biocompatibility:Review and Perspectives. Nov. 2011.*
Trudermis Product Information from olypus Terumo Biomaterials 2011.*
Sigma Aldrich Calf Collagen.*
Azevedo et al. "Understanding the Enzymatic Degradation of Biodegradable Polymers and Strategies to Control Their Degradation Rate". 2004.*
Malvern "Dynamic Light Scattering Common Terms Defined" (2011).*
Artefill Instructions for Use; from Suneva Medical, Inc., www.artefill.com; 12 pages; 7130REV01 (Feb. 20, 2010).
ArteFill Patient Label; from Suneva Medical; www.artefill.com; 6 pages; 7175REV00.
Artefill Skin Test Instructions for Use; from Suneva Medical, Inc. www.artefill.com; 6 pages; 7133REV01(Feb. 2010).
Cheema et al; Collagen: Applications of a Natural Polymer in Regenerative Medicine, Regenerative Medicine and Tissue Engineering—Cells and Biomaterials, Prof. Daniel Eberli (Ed.), ISBN: 978-953-307-663-8, Ipp 288-300; ISBN: 978-953-307-663-8, (2011).
Gautieri et al.; "Hierarchical Structure and Nanomechanics of Collagen Microfibrils from the Atomistic Scale Up"; Nano Letters; 11; pp. 757-766; (2011).
Lemperle et al.; "Soft Tissue Augmentation With Artecoll: 10-Year History, Indications, Techniques, and Complications"; Dermatologic Surgery; 29; pp. 573-587; (2003).
Maier et al.; "Enzyme-Assisted Purification of Denatured Atelocollagen, Using Pronase as Scavenging Agent" Rev. Med. Chir. Soc. Med. Nat., Iasi. 114(4);pp. 1232-1239; (2010), abstract.
Terudermis Product Information from Olympus Terumo Biomaterials Corp.; http://www.biomaterial.co/jp/en/products/terudermis/product.html; 3 pages; copyright 2011; printed Mar. 13, 2014.
Toroian et al; "The Size Exclusion Characteristics of Type I Collagen: Implications for the Role of Noncollagenous Bone Constituents in Mineralization"; The Journal of Biological Chemistry; 282(31); pp. 22437-22447; (2007).
Zhang et al; "Physicochemical Properties of Collagen, Gelatin and Collagen Hydrolysate Derived from Bovine Limited Split Wasts"; Journal of the Society of Leather Technologists and Chemists; 90; pp. 23-26; (2005).
International Search Report and Written Opinion; International Application No. PCT/US2015/020384; International Filing Date Mar. 13, 2015; Date of Mailing Jun. 2, 2015; 12 pages.

* cited by examiner

*Primary Examiner* — Robert A Wax
*Assistant Examiner* — Danah Al-Awadi
(74) *Attorney, Agent, or Firm* — Cantor Colburn LLP

(57) ABSTRACT

Described herein are injectable alloplastic implant compositions that are particularly useful for soft tissue defect augmentation. The compositions include microparticles, such as polymethylmethacrylate particles, and collagen as a suspending agent, wherein the collagen contains a reduced amount of low molecular weight gelatine compared to high molecular weight collagen. By controlling the molecular weight of the collagen in the compositions, the injectability, stability, and antigenicity of the alloplastic implant compositions can be improved.

9 Claims, No Drawings

INJECTABLE ALLOPLASTIC IMPLANTS AND METHODS OF USE THEREOF

CROSS-REFERENCE TO RELATED APPLICATIONS

This application is a continuation of U.S. application Ser. No. 14/211,994 filed on Mar. 14, 2014, which is incorporated herein by reference in its entirety.

FIELD OF THE DISCLOSURE

The present disclosure is related to injectable alloplastic implants and methods of filling defects such as facial defects.

BACKGROUND

Augmentation of soft tissue, e.g., skin, can be employed in many situations, including recovery from injury and for cosmetic or supporting purposes. For example, with normal aging, skin may become loose or creases can form, including, for example, nasal-labial folds, wrinkles, pitting and defects. Soft tissue augmentation can be used to correct defects such as creases and lines, and to counteract the effects of aging. It is desirable to even out irregularities of the skin permanently and without side effects. Soft tissue augmentation is achieved by the use of such materials as collagen, silicone, poly-lactic acid, polyethylene, polytetrafluoroethylene, and hydrogel-based polymer compositions. These materials can be in various forms depending on the use; for example, they can be in the form of thick solutions, gels or suspensions and used as implants or carriers for delivering the implants. Ideal materials for soft tissue augmentation should be sufficiently durable and remain in position and should not migrate from the implantation site.

Injectable dermal fillers are particularly desirable as a non-invasive intervention for reducing the appearance of skin defects. Injectable dermal fillers raise the skin within the skin defect, which is lower or deeper than the surrounding skin, causing the defect to fill to the same level as the surrounding skin, reducing the visibility of the defect.

U.S. Pat. No. 5,344,452 describes an alloplastic implant that is biocompatible and remains permanently at the injection site with substantially no side effects. The implant composition comprises solid particles having a smooth surface and being free from corners and edges such as a biocompatible solid in powder form, in particular polymethyl methacrylate (PMMA), in the form of microparticles. In certain aspects, the implant composition includes a physiologically acceptable suspending agent or carrier such as a biodegradable gelatine, water and/or alcohol. Such a dermal filler is commercially available as Artefill®.

While the compositions of U.S. Pat. No. 5,344,452 are well-suited for their intended purpose, it is desirable to design implant compositions with improved physical properties such as injectability and storage stability.

BRIEF SUMMARY

In one aspect, an alloplastic implant composition comprises microparticles having a diameter of about 5 to about 400 μm suspended in an aqueous suspending agent, wherein the aqueous suspending agent comprises denatured atelocollagen, wherein the denatured atelocollagen has less than 40 wt % of the total weight as components of weight average molecular weight (Mw) 100,000 Daltons or lower.

In another aspect, a method of augmenting a soft tissue defect comprises injecting an alloplastic implant composition near the soft tissue defect, wherein the alloplastic implant composition comprises denatured atelocollagen that has less than 40 wt % of the total weight as components of weight average molecular weight (Mw) 100,000 Daltons or lower.

In a further aspect, a method of improving the injectability of an injectable alloplastic implant composition comprises forming the injectable alloplastic implant composition comprising microparticles having a diameter of about 5 to about 400 μm suspended in an aqueous suspending agent, wherein the aqueous suspending agent comprises denatured atelocollagen, wherein the denatured atelocollagen has less than 40 wt % of the total weight as components of weight average molecular weight (Mw) 100,000 Daltons or lower.

DETAILED DESCRIPTION

Described herein are injectable alloplastic implant compositions that are particularly useful for soft tissue defect augmentation. In one aspect, the compositions include collagen. In a specific aspect, the compositions include microparticles, such as polymethylmethacrylate particles, and a suspending agent comprising collagen, wherein the collagen contains a reduced amount of gelatine compared to high molecular weight collagen. Specifically, the microparticles are suspended in an aqueous suspending agent which is an aqueous collagen solution. In an embodiment, an alloplastic implant composition comprises microparticles having a diameter of about 5 to about 400 μm suspended in an aqueous suspending agent comprising denatured atelocollagen, wherein the denatured atelocollagen has less than 40 wt % of the total collagen weight as components of weight average molecular weight (Mw) 100,000 Daltons or lower. In one aspect, the denatured atelocollagen has 60 wt % or greater, specifically 60 to 100 wt %, components of weight average molecular weight 100 kDa to 258 kDa. Optionally, the polydispersity of the denatured atelocollagen expressed as Mw/Mn is 1.0 to 1.6, wherein Mw is weight average molecular weight and Mn is number average molecular weight. It was unexpectedly found that when collagen contains a significant fraction of low molecular weight gelatine (e.g., less than 100 kDa or even much smaller), the resulting implant compositions can have reduced gel strength as well as reduced storage stability. In addition, the low molecular weight gelatine component of the collagen contributes to difficulty in injecting the compositions as noted in the background of U.S. Pat. No. 5,344,452. The reduction of the amount of the low molecular weight components of the collagen is also expected to reduce the immunological response to the alloplastic implant compositions that can occur upon injection into a human subject.

Without being held to theory, it is believed that denatured atelocollagen having 60 wt % or greater components of weight average molecular weight 100 kDa or higher as described herein allows for improved water junction formation and subsequent physical properties for use in an alloplastic implant that were not previously achieved. The improved properties may include, but are not limited to, broad range temperature stability, constant flow rheological characteristics, superior microparticle suspending properties, and maintained homogeneous microparticle distribution during storage within holding vials and/or syringe-like delivery vehicles. In certain aspects, the denatured atelocollagen has less than 40 wt % of the total collagen weight as components of weight average molecular weight (Mw) of less than 80 kDa, less than 60 kDa, less than 40 kDa or less than 20 kDa. In another aspect, the denatured atelocollagen has greater than 60% of the total weight as components of weight average molecular weight (Mw) of greater than 120 kDa, 150 kDa, 160 kDa, 175 kDa, 180 kDa or 200 kDa. In a yet further aspect, the denatured atelocollagen has less than 30 wt %, 25 wt %, 20 wt %, 15 wt %, 10 wt % or 5 wt % of the total collagen weight as components of weight average molecular weight (Mw) of less than 100 kDa. In a still further aspect, the denatured atelocollagen has 60 wt % or greater, 70 wt % or greater, 75 wt % or greater, 80 wt % or greater, 85 wt % or greater, 90 wt % or greater or 95 wt % or greater, components of weight average molecular weight 100 kDa to 258 kDa. In one aspect, the denatured atelocollagen is prepared from bovine or porcine collagen.

As used herein, the term microparticle refers to small particles that have a substantially smooth surface and that are free from corners, edges and the like. In other words, the particles do not have sharp transitions at their surfaces such as would be found at corners and edges. In addition, the particles do not have peaks or tapered projections. In one aspect, the surface does not contain pores. Due to the smooth and smoothed off surface structure, no cells and other tissue structures are damaged when the microparticles are injected into soft tissue. In addition, the danger of causing reactions of the tissue, which are followed by infections, is minimized.

In one aspect, the microparticles are dynamically balanced solid particles, and in particular particles having an elliptical or spherical form. In addition, it is possible to use solid particles of different geometrical forms if substantially all the particles have a smooth or smoothed-off surface.

The microparticles have an average diameter of about 5 to about 400 μm, specifically about 10 to about 200 μm, and more specifically about 15 to about 60 μm. As used herein, the term "about" means ±10%. If the microparticles do not have a spherical form, then the diameter refers to the greatest diameter of the smallest cross sectional area. Such solid particles are too large to be "eaten" by monocytes. Due to the form, surface and size of the particles, they are not detected by the endogenous macrophages as foreign bodies, so no defensive reactions take place. In addition, the microparticles are small enough to be injected through a cannula of an injection syringe to the desired site. Microparticles having the diameters specified above cannot be identified by touch as a single foreign body in or under the skin. Advantageously, the microparticles have a diameter such that they are not washed away through lymph tracts or other tissue tracts from the site to which they have been administered. In addition, microparticles having a spherical form or a spherical-like form have the advantage that they form a closely packed arrangement at the site where they have been placed.

The microparticles are composed of an inert, histocompatible material such as glass. In another aspect, the solid particles are composed of a polymer, and in particular a completely cured and fully polymerized polymer so that no remaining monomers, which may be toxic or may cause cancer, are incorporated into the body of the treated patient. It is possible to use any inert histocompatible polymer/copolymer for producing the microparticles.

Exemplary polymers include substituted and unsubstituted polymethyacrylates, sodium acrylate polymers, acrylamide polymers, acrylamide derivative polymer or copolymers, sodium acrylate and vinyl alcohol copolymers, vinyl acetate and acrylic acid ester copolymers, vinyl acetate and methyl maleate copolymers, isobutylene-maleic anhydride crosslinked copolymers, starch-acrylonitrile graft copolymers, crosslinked sodium polyacrylate polymers, crosslinked polyethylene oxide, acrylate/methacrylate copolymers, and mixtures thereof. In one embodiment, the microparticles comprise a polymer or copolymer comprising a methacrylate monomer such as a methylmethacrylate monomer.

In one aspect, polymethacrylates and in particular polymethylmethacrylate (PMMA) is used as the polymer for the microparticles. Fully polymerized PMMA is histocompatible and is chemically and physically inert in the human body. PMMA is used in manufacturing implants, for instance for the plastic covering of bone defects in the face and in the cranium or as an arthroplasty. PMMA is also used for the manufacturing artificial teeth, as suture material and for manufacturing intraocular lenses and dialysis membranes.

In order to inject the microparticles as an implant in or under the skin, the microparticles are suspended in an aqueous suspending agent. In one aspect, the aqueous suspending agent has a pH of 6.0 to 8.0, and includes, for example, a salt such as sodium chloride and a buffer such as a phosphate buffer. The suspending agent includes denatured atelocollagen as described herein such as denatured atleocollagen having 60 wt % or greater components of weight average molecular weight 100 kDa or higher. In one aspect, the denatured collagen comprises 0.5 to 15 wt % of the suspending agent, specifically 1 to 10 wt %, more specifically 3 to 5 wt % and most specifically 3.5 wt % of the suspending agent. An exemplary suspending agent includes 3.5 wt % denatured atelocollagen, 0.3 wt % lidocaine hydrochloride, 2.7 wt % phosphate buffer, 0.9 wt % sodium chloride and 92.6 wt % water for injection.

Collagen, atelocollagen, and gelatine are physically and structurally different and these differences manifest themselves in various physical properties that are important when evaluating viable biomaterials that may be used as suspending agents for dermal filling and corrective treatment of tissue defects, such as wrinkles and scars. Collagen is the primary structural protein of connective tissue in animals and is the most abundant protein in mammals. Collagen is composed of a triple helix with two identical chains (α1) and a third chain that differs slightly in its chemical composition (α2). Collagen sequences are well-known in the art and the most abundant sequences are glycine-proline-X and glycine-X-hydroxyproline. Collagen can be isolated from a variety of animal sources and includes, for example, bovine collagen. Collagen also includes recombinant collagen. Atelocollagen is a water-soluble form of collagen formed through treatment of collagen with proteases. Gelatine is derived through partial hydrolysis of the collagen extracted from animal skin, bones, cartilage, ligaments, etc. Denatured collagen, such as denatured atelocollagen, refers to substantially single-stranded collagen, specifically collagen containing greater than 90% single strands. Denatured collagen is produced by, for example, alkali-enzyme techniques.

While collagen and gelatine have been used previously in the field of soft tissue augmentation, the molecular weight of the collagen and gelatine is rarely identified. In general, intact collagen has a molecular weight distribution including fractions of 100 kDa and below, as well as 200 kDa molecular weight fractions and even 250,000 Dalton molecular weight fractions. The average molecular weight of collagen is about 300 kDa, although individual preparations have lower molecular weights due to degradation of the collagen chains, for example. Atelocollagen generally has an average molecular weight of 258 kDa. Irreversible gelatine has an average molecular weight of about 2,000 Daltons. Unless indicated otherwise, molecular weight as used herein refers to weight average molecular weight.

As noted in the background of U.S. Pat. No. 5,344,452, while gelatine is a biodegradable protein that is useful in compositions to even out skin irregularities, gelatine can be extremely difficult to inject. In the Artefill® product, bovine collagen is used instead of gelatine as it is also biodegradable and is further easier to inject. However, it has been discovered that preparations of collagen such as bovine collagen contain a distribution of molecular weights, including a low molecular weight gelatine component. Without being held to theory, it is believed that the gelatine component of collagen preparations contributes to challenges with injection/extrusion force and also causes immunological responses. In order to improve the functionality of the suspending agent to provide improved injectability and extrusion force, improved gel strength, facilitate room temperature stability, as well as prevent microparticles from aggregating at temperature elevated above 2-8° C., the gelatine component of collagen preparations should be eliminated.

The gelatine (i.e., low molecular weight components) can be removed from collagen preparations by techniques known in the art such as dialysis or size exclusion chromatography. In one embodiment, the collagen is bovine or porcine collagen. The collagen an also be crosslinked with glutaraldehyde, including lightly crosslinked collagen.

In addition to the collagen, the aqueous suspending agent can include alcohols such as ethyl alcohol, and/or a tenside such as Tween® 80 as well as mixtures thereof. Tween® 80 is a polyethoxysorbitanoleate. It is not only possible to use the mentioned Tween® type (Tween 80) but also other Tween® types. The tenside changes the surface tension of water so that the solid particles and in particular the polymer particles float better.

In another embodiment, the suspending agent further comprises sodium hyaluronate or crosslinked sodium hyaluronate.

The mixing ratio of the components of the suspending agent can be chosen according to the needs and in particular according to the size of the syringe used for the injection.

In one embodiment, the alloplastic implant composition has improved stability, for example, the microparticles are stable for at least 30 days at a temperature of 20 to 25° C. As used herein, the term stable means that the microparticles do not agglomerate and/or aggregate when suspended in an aqueous dispersion containing the suspending agent described herein. In one aspect, the suspending agent described herein provides a stable suspension over a wide range of temperatures, such as 2 to 25° C.

By using the suspending agent disclosed herein, it is easier to inject the solid particles as with the help of an injection syringe, for instance intracutenously. It is for instance possible to use a 20 to 30 gauge, specifically a 26 or 27 gauge needle for such an injection. A 26 gauge needle has a 0.45 mm outer diameter, and a 27 gauge needle has a 0.4 mm outer diameter.

In another embodiment, a method of improving the injectability of an injectable alloplastic implant composition comprises forming the injectable alloplastic implant composition comprising microparticles having a diameter of about 5 to about 400 nm suspended in an aqueous suspending agent, wherein the aqueous suspending agent comprises denatured atelocollagen, wherein the denatured atelocollagen has less than 40 wt % of the total weight as components of weight average molecular weight (Mw) 100,000 Daltons or lower.

One disadvantage of the Artefill® product is that a skin test is required prior to use because the product contains bovine collagen and is contraindicated in subjects with allergies to bovine collagen products. Without being held to theory, it is believed that because the collagen used in the alloplastic implant compositions described herein do not contain the low molecular weight gelatine component, the risk of an adverse allergic response is reduced. Thus, in one embodiment, a skin test to determine sensitivity to the collagen in the alloplastic implant composition is not required prior to use.

The compositions can further include one or more active agents such as one or more local anesthetics such as lidocaine, anti-inflammatory agents, tissue formation agents, adipose tissue formation agents, anesthetics, antioxidants, heparin, epidermal growth factor, transforming growth factor, transforming growth factor-β, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons or combinations thereof. Additional active agents include glucosaminoglycans, fibronectins, lectins, polycations (such polylysine, chitosan and the like), surface receptor binding motifs like arginine-glycine-aspartic acid (RGD), growth factors like basic fibroblast growth factor (bFGF), platelet derived growth factor (PDGF), transforming growth factor (TGF), cytokines like tumor necrosis factor (TNF), interferon (IFN), interleukins (IL), and structural sequences including elastin, hyaluronic acid and others. Additionally recombinant, synthetic, or non-native polymeric compounds might be used as decoration including chitin, poly-lactic acid (PLA), and polyglycolic acid (PGA). Other active agents include tracers, and contrasting agents. The compositions can further comprise one or more cells or tissues, such as adipose tissue or dermal fibroblasts. In one aspect, the cells are autologous cells.

In one embodiment, a method of filling a soft tissue defect comprises injecting an alloplastic implant composition near the soft tissue defect, wherein the alloplastic implant composition comprises denatured atelocollagen that has less than 40 wt % of the total weight as components of weight average molecular weight (Mw) 100,000 Daltons or lower. In one aspect, the denatured atelocollagen is in the form of suspending agent and the alloplastic implant composition further has suspended therein microparticles having a diameter of about 5 to about 400 µm.

In certain aspects, the denatured atelocollagen has less than 40 wt % of the total collagen weight as components of weight average molecular weight (Mw) of less than 80 kDa, less than 60 kDa, less than 40 kDa or less than 20 kDa. In another aspect, the denatured atelocollagen has greater than 60 wt % of the total weight as components of weight average molecular weight (Mw) of greater than 120 kDa, 150 kDa, 160 kDa, 175 kDa, 180 kDa or 200 kDa. In a yet further aspect, the denatured atelocollagen has less than 30 wt %, 25 wt %, 20 wt %, 15 wt %, 10 wt % or 5 wt % of the total collagen weight as components of weight average molecular weight (Mw) of less than 100 kDa. In a still further aspect, the denatured atelocollagen has 60 wt % or greater, 70 wt % or greater, 75 wt % or greater, 80 wt % or greater, 85 wt % or greater, 90 wt % or greater or 95 wt % or greater, components of weight average molecular weight 100 kDa to 258 kDa. In one aspect, the denatured atelocollagen is prepared from bovine collagen or porcine collagen.

In one embodiment, the alloplastic implant composition as described herein is injected near a soft tissue defect in a human subject to augment the soft tissue defect. The alloplastic implant composition may be injected below the soft tissue defect at a junction of the dermis and subcutaneous fat to augment soft tissue and to provide long-term reduction of a skin defect. In one aspect, injection is performed using a tunneling technique in which the needle is moved back and forth below the scar. In general, pressure is applied during the entire injection process.

In one aspect, the soft tissue defect is the result of aging including premature aging. Aging can be a result of loss of collagen and hyaluronic acid in the skin during the aging process or a result of premature aging caused by, for example, overexposure to sunlight, overexposure to environmental pollutants, smoking tobacco products, exposure to cigarette smoke, poor nutrition and/or skin disorders. In one aspect, the soft tissue defect is a nasolabial fold, also known as "smile lines" or "laugh lines."

In another embodiment, the soft tissue defect is a wrinkle, such as a dynamic wrinkle, a fine wrinkles or a static wrinkle. Dynamic wrinkles include a forehead crease, a brow burrow or an eye line (crow's feet). Static wrinkles include skin fold wrinkle resulting from sagging skin.

In another embodiment, the soft tissue defect is a scar such as an acne scar, a "rolling" scar, a "boxcar" scar or an "ice pick" scar, a surgical scar, trauma scar, a large pore and a soft tissue contour defect.

In another aspect, the soft tissue defect can be caused by a medical condition resulting in a deformity that requires re-contouring, such as a small tissue defect (e.g., after animal bite(s)) or a deformity related to trauma where the deformity is cosmetically unappealing. In a further embodiment, augmentation may be after plastic surgery to achieve symmetry or a desired result.

As used herein, a "long-term" reduction of a soft tissue defect is of a duration of at least one year, specifically one year to about five years, more specifically about five years to about ten years, and most specifically about ten years or longer.

In one embodiment, injection of the alloplastic implant composition is repeated at 2 week intervals until the desired level of correction is achieved.

The invention is further illustrated by the following non-limiting examples.

EXAMPLES

Characterization of Collagen

Using laser light scattering in conjunction with an Opti-lab™ refractive index detector and a QELS measurement, soluble collagen was studied to determine absolute molar mass moments (Mn, Mp, Mw and Mz) the polydispersity (Mw/Mn and Mz/Mn) the rms radius moments (Rn, Rw and Rz), the hydrodynamic volume, and the presence of aggregates which is the assembly high molecular byproducts of the manufacturing process of the starting manufacturing material of bovine hides, specifically Type 1 collagen. The results of testing of prior Artifill® collagen samples showed a polydispersity and molecular weight distribution that contained majority fractions, depending on sample tested, to be 40 to 80 percent (%) at approximately 100K daltons (Mw), or less. Additionally, Rz values for the hydrodynamic radius showed three of the four Artifill® collagen samples tested with low numerical values indicating compacted three dimensional space occupation, such that influence of the low weight average molecular weight could be seen further differentiated from the higher Mw sample tested. The tests further indicated single strand composition as part of the overall product make-up. The lowest Mw component does not favorably influence stability or the strength of the carrier gel properties and subsequent performance.

| Sample ID | Avg. Molecular Weight (Mw) Gm/Mol kD | Rz | Calculated Mass by Astra µg |
|---|---|---|---|
| Collagen (Knox gelatin) | 182K | 45 | 197 |
| Artefill received in 50 cc syringed on Aug. 28, 2013 Lot# | 183K | 49 | 53 |
| Artefill Collagen Lot# F131056 received Oct. 11, 2013 (sample 5) | 241K | 60 | 216 |
| Artefill Collagen Lot# F131056 received Oct. 11, 2013 (sample 6) | 104K | 41 | 135 |

| Prior Art Artefill Collagen Sample 1- atelocollagen | |
|---|---|
| Number average molecular weight (Mn) | 147 kDa |
| Weight average molecular weight (Mw) | 240 kDa |
| Polydispersity as Mw/Mn | 1.638 |
| % of molecular weights less than 100 kDa | 60% |
| Prior Art Artefill Collagen Sample 2- atelocollagen | |
| Number average molecular weight (Mn) | 70 kDa |
| Weight average molecular weight (Mw) | 103.5 kDa |
| Polydispersity as Mw/Mn | 1.481 |
| % of molecular weights less than 100 kDa | 80% |
| Gelatin sample- Knox gelatin 180-185 kDa (not denatured) | |
| Number average molecular weight (Mn) | 120 kDa |
| Weight average molecular weight (Mw) | 188 kDa |
| Polydispersity as Mw/Mn | 1.488 |
| % of molecular weights less than 100 kDa | <10% |
| Inventive Example- 3.5 wt % denatured atelocollagen | |
| Number average molecular weight (Mn) | 151 kDa |
| Weight average molecular weight (Mw) | 183 kDa |
| Polydispersity as Mw/Mn | 1.211 |
| % of molecular weights less than 100 kDa | 40% |

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. As used herein, wt % means percent by weight. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An alloplastic implant composition comprising
   microparticles having a diameter of about 5 to about 400 μm suspended in
   an aqueous suspending agent, wherein the aqueous suspending agent comprises denatured atelocollagen, wherein the denatured atelocollagen has less than 10 wt % of the total weight as components of weight average molecular weight (Mw) 100,000 Daltons or lower, and greater than 70 wt % components of weight average molecular weight 100 kDa to 258 kDa,
   wherein the polydispersity of the denatured atelocollagen expressed as Mw/Mn is 1.0 to 1.6, wherein Mw is weight average molecular weight and Mn is number average molecular weight.

2. The alloplastic implant composition of claim 1, wherein the denatured atelocollagen is prepared from bovine or porcine collagen.

3. The alloplastic implant composition of claim 1, wherein the pH of the aqueous suspending agent is 6.0 to 8.0 and the concentration of denatured atelocollagen in the aqueous suspending agent is 0.5 to 15 wt %.

4. The alloplastic implant composition of claim 1, wherein the microparticles have a diameter of about 10 to about 200 μm.

5. The alloplastic implant composition of claim 1, wherein the microparticles comprise a polymer or copolymer comprising a methacrylate monomer.

6. The alloplastic implant composition of claim 5, wherein the polymer or copolymer is polymethylmethacrylate.

7. The alloplastic implant composition of claim 1, wherein the composition is injectable through a 20 to 30 gauge needle.

8. The alloplastic implant composition of claim 1, further comprising an anesthetic.

9. The alloplastic implant composition of claim 1, wherein the suspension is stable for at least 30 days at a temperature of 20-25° C.

* * * * *